US 6,673,038 B2

(12) United States Patent
Weston

(10) Patent No.: US 6,673,038 B2
(45) Date of Patent: Jan. 6, 2004

(54) NEEDLELESS INJECTOR CARTRIDGE

(75) Inventor: Terence Edward Weston, Stradbroke (GB)

(73) Assignee: Aradigm Corporation, Hayward, CA (US)

( * ) Notice: Subject to any disclaimer, the term of this patent is extended or adjusted under 35 U.S.C. 154(b) by 0 days.

(21) Appl. No.: 09/794,768

(22) Filed: Feb. 26, 2001

(65) Prior Publication Data
US 2001/0027290 A1 Oct. 4, 2001

Related U.S. Application Data

(63) Continuation of application No. PCT/GB99/02881, filed on Sep. 1, 1999.

(30) Foreign Application Priority Data

Sep. 15, 1998 (GB) .............................. 9819962

(51) Int. Cl.[7] .................. A61M 37/00; A61M 5/30; A61M 25/16; A61M 25/18; A61M 5/32
(52) U.S. Cl. .................. 604/88; 604/68; 604/535; 604/539; 604/414
(58) Field of Search .................. 604/187, 68, 82, 604/83, 86, 87, 88, 89, 91, 92, 533, 534, 535, 539, 411, 414, 415

(56) References Cited

U.S. PATENT DOCUMENTS

| 3,948,266 | A | * | 4/1976 | Clark et al. ............... 604/72 |
| 4,010,747 | A | | 3/1977 | Clark et al. ............... 128/173 H |
| 4,338,980 | A | | 7/1982 | Schwebel et al. ......... 141/18 |
| 4,439,184 | A | * | 3/1984 | Wheeler .................... 604/191 |
| 5,062,830 | A | | 11/1991 | Dunlap ...................... 604/68 |
| 5,649,912 | A | * | 7/1997 | Peterson .................... 604/187 |
| 5,891,086 | A | * | 4/1999 | Weston ...................... 604/70 |
| 6,174,304 | B1 | * | 1/2001 | Weston ...................... 604/201 |
| 6,280,410 | B1 | * | 8/2001 | Weston et al. ............. 604/232 |

FOREIGN PATENT DOCUMENTS

| CA | 1258019 | 8/1989 |
| EP | 0 737 484 1 | 4/1996 |
| WO | WO 89 08469 | 9/1989 |
| WO | WO 94 01150 | 1/1994 |
| WO | WO 95 24176 | 9/1995 |
| WO | WO 95 24176 A | 9/1995 |
| WO | WO 96 15821 A | 5/1996 |
| WO | WO 96 19252 | 6/1996 |
| WO | WO 97 22375 A | 6/1997 |
| WO | WO 97 25015 | 7/1997 |
| WO | WO 98 12121 A | 3/1998 |

* cited by examiner

Primary Examiner—Manuel Mendez
Assistant Examiner—Mark K. Han
(74) Attorney, Agent, or Firm—Carol M. LaSalle; Bozicevic, Field & Francis LLP

(57) ABSTRACT

A needleless injector cartridge, comprises an injection component (1) defining a void (17) therein for receiving medicament, and having an injection discharge orifice communicating with the void. The cartridge further comprises a transfer device (2) comprising a liquid-containing reservoir (4), and transfer means for causing the liquid (5) to flow from the reservoir, through a reservoir outlet, into the void in the injection component.

16 Claims, 6 Drawing Sheets

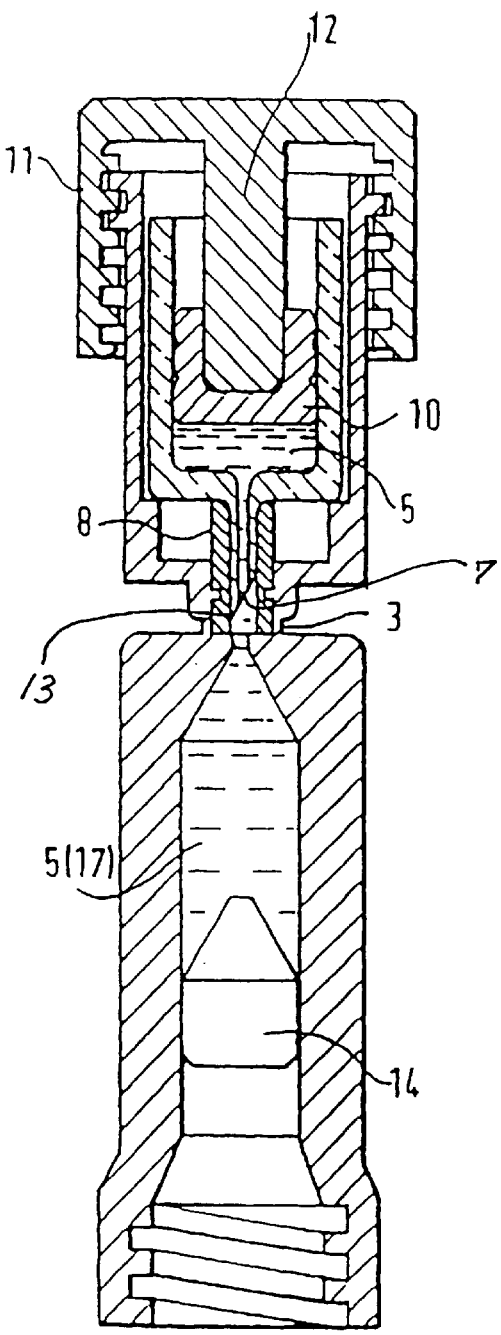
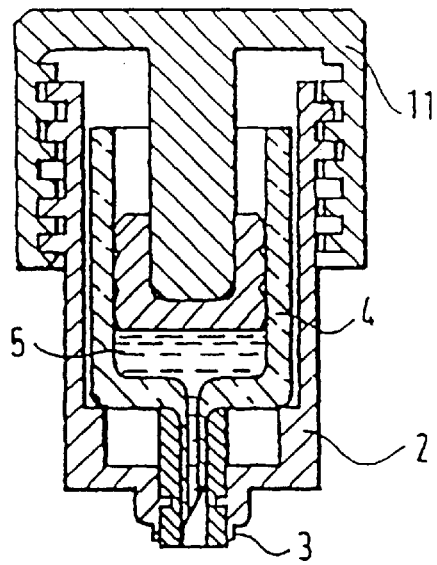
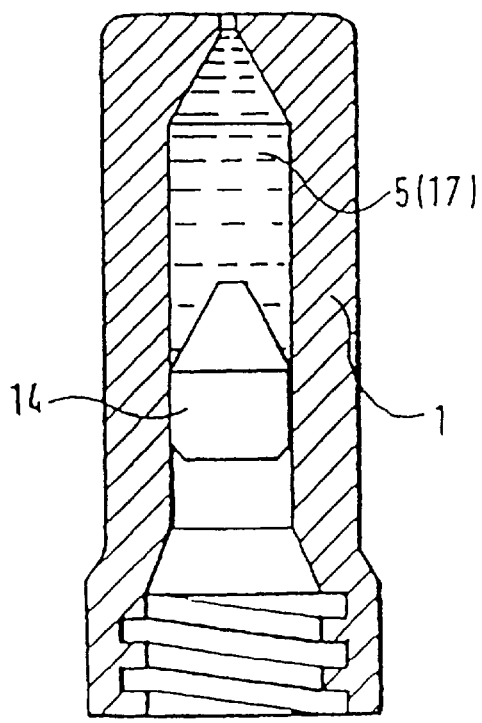
Fig. 6.
Fig. 7.

NEEDLELESS INJECTOR CARTRIDGE

This is a continuation of international application Ser. No. PCT/GB99/02881, filed Sep. 1, 1999, the entire disclosure of which is hereby incorporated by reference.

This invention relates to needleless injector cartridges.

Needleless injectors are used as an alternative to conventional hypodermic syringes for injecting liquid medicaments into the tissues of a patient. The usual principle of operation is a high pressure piston pump which propels a jet of liquid with sufficient force to penetrate the epidermis and deposit in the underlying tissues. Such devices have been available for over fifty years and most examples are multi-dose devices—that is, a succession of doses may be drawn from a reservoir, each dose being dispensed from an integral pressure chamber. The motive force may be derived from stored electrical, manual, pyrotechnic or pressurised gas energy.

In the 1980's, there were some reports of cross contamination through using multi-dose injectors, which promoted a search for safer ways, and a variety of injectors were invented comprising a multi-dose power unit or actuator, to which a disposable injection cartridge could be fixed. These cartridges were usually intended to be filled by the user with the aid of a transfer device, by which means a medicament could be drawn from a vial and transferred to a cartridge. There are a number of problems arising from this approach: it is practically impossible to achieve aseptic transfer of the medicament; there is likelihood of significant amounts of trapped air bubbles in the cartridge which reduce injection performance; and there is a chance of preparing an incorrect amount to be injected. A few attempts were made to supply prefilled cartridges, but most materials proposed for the cartridges were unsuitable for long-term contact with the medicament, or at least would require extensive and costly validation for each application.

The ideal material for most applications is borosilicate glass, because it has the required inertness, transparency, and barrier properties. However, the pressures reached in needleless injectors can be very high—in the order of 600 bars—and a cartridge to be made from glass requires very careful design and processing in order to avoid breakage. Our co-pending application published under No. WO 98/13086 describes a method of manufacturing glass needleless injector cartridges, but the process requires a large investment in specialised plant in order to achieve the low component cost necessary for many applications.

Some drugs cannot be stored for long periods in glass however, and therefore have to be stored in some other material. In such cases, that other material will still be unlikely to withstand the high injection pressures.

The present invention seeks to overcome the drawbacks of prior art devices by providing a needleless injector cartridge which includes a liquid medicament reservoir as an attached part thereof, with means to transfer the liquid from the reservoir into the part of the cartridge from which injection takes place.

In accordance with the invention there is provided a needleless injector cartridge, comprising:
   an injection component defining a void therein for receiving medicament, and having an injection discharge orifice communicating with the void; and
   a transfer device comprising a liquid-containing reservoir, and transfer means for causing the liquid to flow from the reservoir, through a reservoir outlet, into said void.

Preferably the reservoir is made of glass, but other materials may be used if glass is unsuitable for long term storage contact with the medicament. The injection component may be of a material suitable for short term contact with the medicament, and suitable for the extremely high injection pressures. Stainless steel or liquid crystal polymer are two diverse materials which would be suitable, or a combination of materials may be used to optimise the requirements of cost, performance and size—for example an inexpensive polypropylene cartridge may be housed in a steel casing, the latter providing support for the plastic during the injection.

In a first preferred embodiment there is provided plastic injection component which is preferably a cylinder containing a piston, and which has a small discharge orifice at one end. Attached, preferably coaxially, to the injection component at the discharge end is an open cylinder into which is placed a reservoir made from a material compatible with the medicament contained therein. The reservoir has a sharp discharge tube at one end, and the other contains a plunger, with the medicament contained between the plunger and discharge tube. An elastomeric seal surrounds and seals on the outside of the discharge tube and also seals against the discharge orifice of the injection component. The seal provides a conduit between the reservoir and injection component, but is temporarily blocked by a septum. The piston in the injection component is located so as to permit the latter to receive the required volume of liquid, and the void between the piston and septum is evacuated. A screw cap on the reservoir holder acts on the plunger in the reservoir, so that when the cap is rotated the plunger drives the reservoir forward until the reservoir discharge tube perforates the septum. Continued movement of the cap dispenses the required volume of medicament from the reservoir into the injection component. The reservoir holder, reservoir, plunger and cap are then detached together and the filled injection component is ready for use. The use of the screw cap enables the user to move the plunger steadily, in a manner which avoids any sudden jerks, thus reducing the possibility of the liquid undergoing undesirable foaming. It also means that a greater force be exerted on the plunger, so enabling a larger diameter plunger to be used than would otherwise be the case. That in turn means that the reservoir can be shorter, so helping to keep the overall length of the transfer device short. The cartridge may be attached to a multi-use actuator or a single use device, or have been pre-assembled to such before filling.

A second preferred embodiment provides a device for transferring a liquid as described in the first preferred embodiment, wherein a lyophilised (freeze dried) drug or other dry material is held within the evacuated injection component, and the transfer of liquid in the described manner dissolves the material so that it may be injected.

A third preferred embodiment is similar to the first, except that the reservoir is fitted with two plungers, spaced apart, and containing the liquid within the space. Forward movement of the plungers brings the liquid up to one or more bypass grooves in the wall of the reservoir, so that the liquid passes through the grooves and into the injection component.

In all of the embodiments described above there is a vacuum within the cartridge, so that the chance of a large gas bubble being trapped is reduced when the liquid is transferred. The piston within the injection component is held in position with sufficient friction to prevent its movement due to the pressure differential. If the existence of bubbles is not particularly important, then a fourth embodiment has the piston placed initially near to the injection discharge orifice of the injection component and when the content of the reservoir is transferred, the piston moves in response to the hydraulic pressure created by the transfer mechanism. This embodiment does not require evacuation of the drug chamber before filling, but if it is necessary to reduce trapped air to a very small volume, evacuating the void within the capsule before filling will achieve this objective.

The invention is described in more detail with reference to the accompanying drawings, all of which are centreline sections of substantially cylindrical devices.

FIG. 6 shows the cartridge after transferring the medicament from the reservoir;

FIG. 7 shows the reservoir components detached from the injection component;

In the interests of clarity, like parts are given like annotation when possible.

Figure 1:
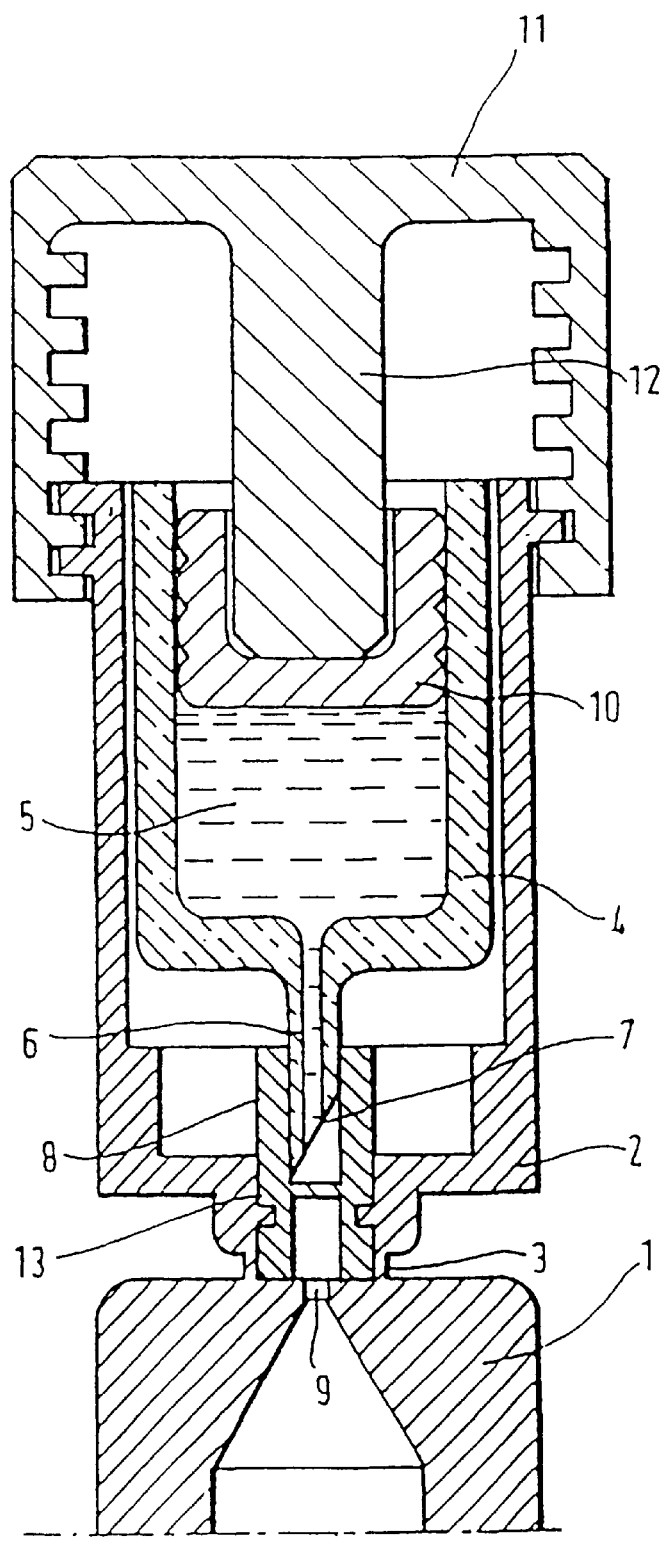
FIG. 1 shows the detachable reservoir.
Figure 2:
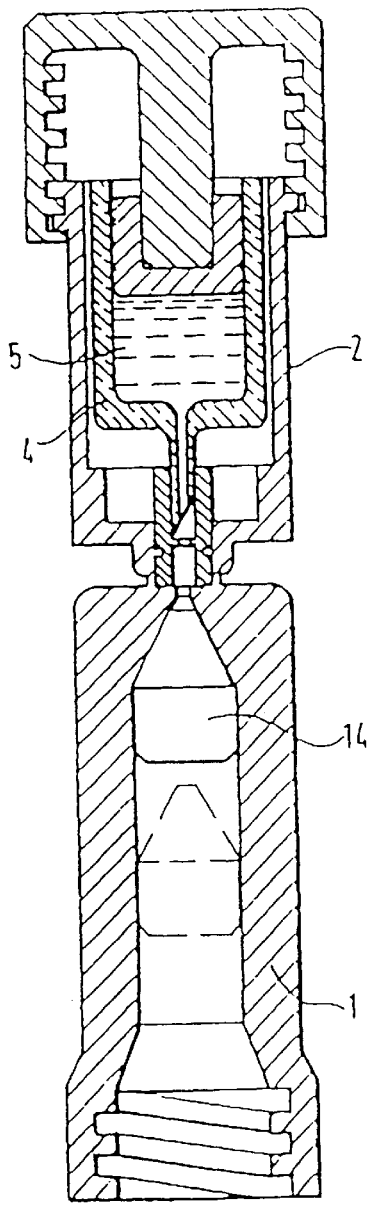
FIG. 2 shows a reservoir and injection component assembly suitable for hydraulic displacement of the piston.

Referring to FIG. 1, injection component 1 for needleless injection has a reservoir holder 2 attached by a frangible connection 3. Located slidingly within the holder 2 is the medicament reservoir 4 containing a liquid medicament 5. A discharge tube 6 is attached to, or integral with, the reservoir 4 is in fluid connection with the medicament 5, and terminates with a sharp bevel 7. A tubular seal 8 protects against the ingress of bacteria both to the medicament 5 and the discharge orifice 9 of the injection component 1. A plunger 10 is sealingly and slidingly assembled into the bore of reservoir 4 and in contact with the medicament 5: preferably there is no (or only a small amount of) trapped air within the medicament 5. A screw cap 11 is assembled to the reservoir holder 2, and has a central rod which engages with the plunger 10. The seal 8 has a septum 13 which, until pierced, prevents the contents of the reservoir 4 from being transferred into the injection component 1.

Figure 4:
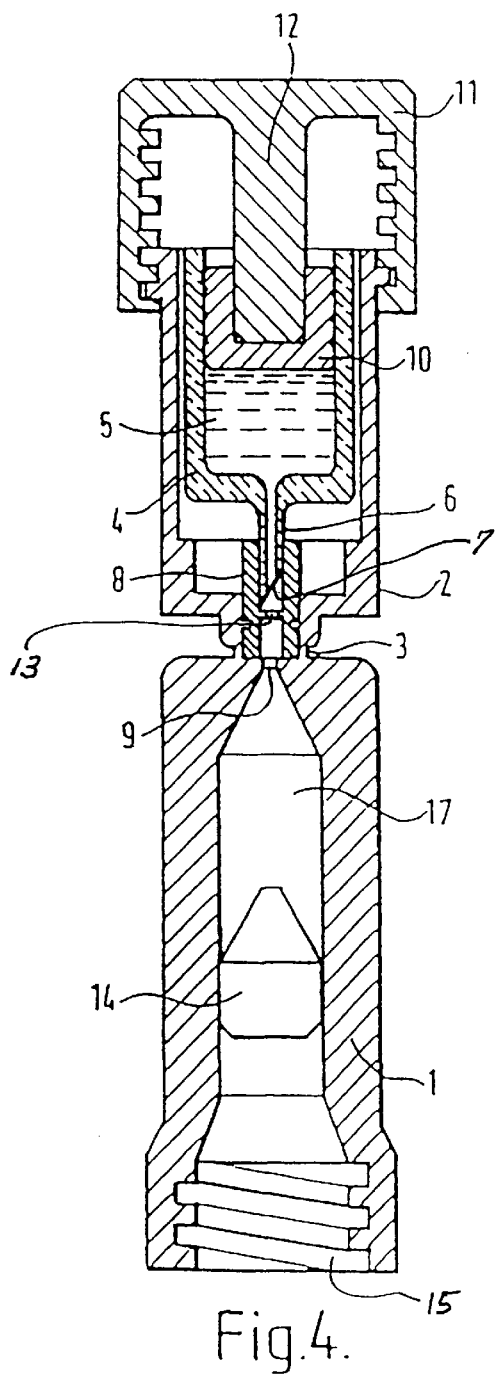
FIG. 4 shows a reservoir and injection component assembly.
Figure 5:
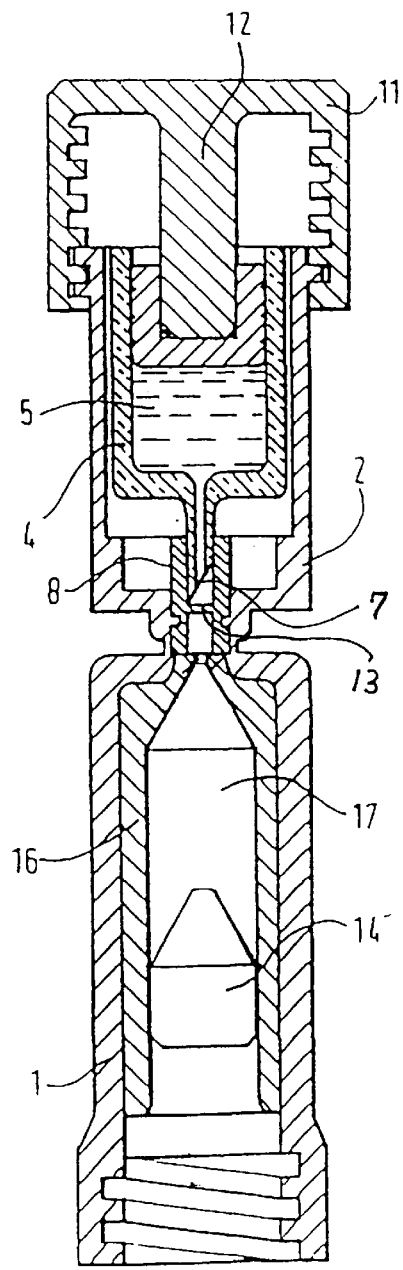
FIG. 5 shows a similar assembly with a separate liner within the injection component body.

Referring to FIG. 4, injection component 1 has a piston 14 sealingly and slidingly assembled therein, and has a screw thread 15 for attachment to a needleless injector actuator or power unit. Alternatively the means of attachment could be a snap, separate clip or other convenient means to facilitate the actual device design and application, or the cartridge could be integral with the power unit. FIG. 5 is similar to FIG. 4 except that the injection component 1 comprises a separate liner 16 fitted therein, in order to provide properties specific to the medicament and the application. In both FIG. 4 and FIG. 5, the void 17 between the piston 14 and the septum 13 is evacuated to, say, 0.1 bar.

FIG. 6 shows the screw cap 11 operated so that the rod 12 has pushed the plunger 10 towards the injection component 1. The medicament 5 is unable to escape, and the entire reservoir 4 therefore moves with the cap 11 and rod 12. When the sharp bevelled end 7 reaches the septum 13, it cuts through and permits the medicament 5 to flow through the bore of the discharge tube 6 and into the void 17 in injection component 1 in liner 16 in FIG. 5. Most of the liquid will be transferred as a result of the pressure differential between the void 17 and the reservoir 4, and continued movement of the plunger 10 completes the transfer of medicament 5. The amount transferred may be controlled by adjusting the screw cap 11 according to volume-related markings (not shown) on the outside of the holder 4, or the piston 14 may reach a stop position determined by a feature within the bore or injection component 1 or the power unit.

After the user has filled the injection component by transfer of liquid from the transfer device, the entire reservoir and associated components are detached from the injection component at the frangible connection 3, as shown in FIG. 7, and the filled injection component is ready for attachment to the power unit. Alternatively, the cartridge may already have been attached to the power unit by the manufacturer (as indicated above the two may for example be integral with one another). The frangible connection 3 may be a feature of a one piece of moulding of the injection component 1 and holder 2, or it may be a separate joining means, the intention being to provide a one-trip device with tamper evidence to prevent misuse or abuse.

U.S. Pat. No. 5,891,086, issued Apr. 6, 1999, the contents of which are incorporated herein by reference, is assigned to the present applicant and discloses a needleless injector suitable for use with the above described injection component.

Figure 3:
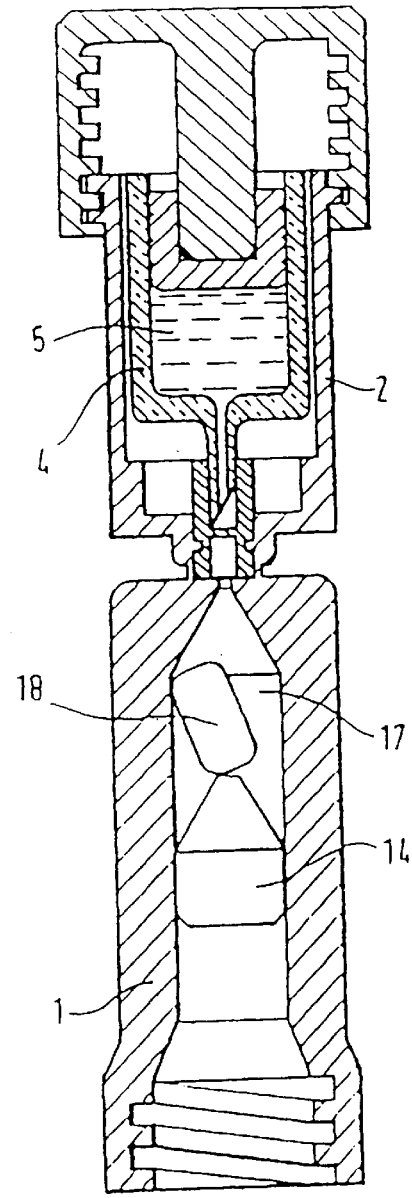
FIG. 3 shows the device with a pellet of lyophilised drug.

Some applications require that a lyophilised drug is reconstituted prior to injection, and FIG. 3 shows an assembly similar to that shown in FIG. 4, but having a pellet of lyophilised material 18 placed within the void 17. Here the vacuum serves to preserve the lyophilised material by preventing hydration.

Figure 8:
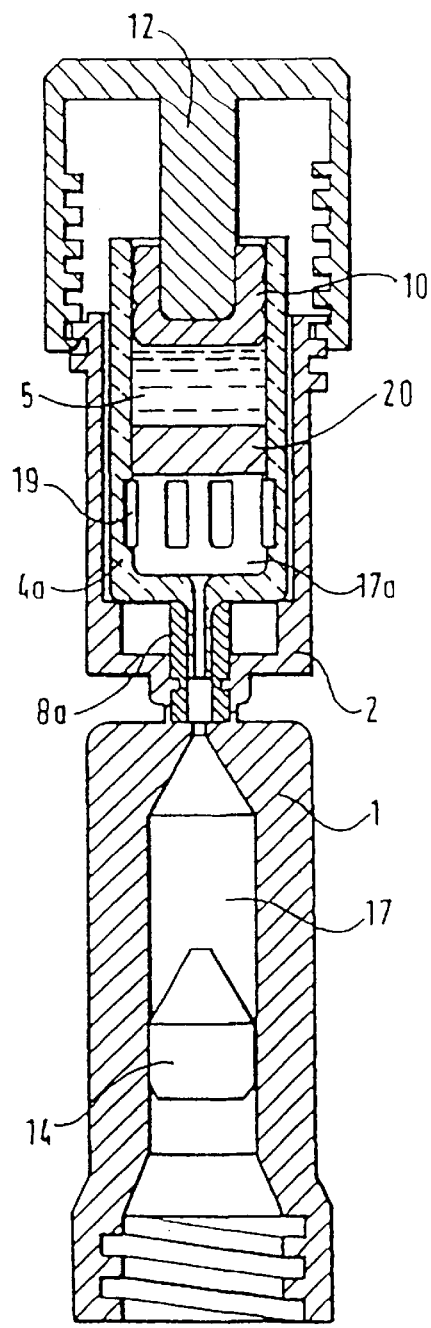
FIGS. 8 and 9 show a bypass embodiment of the invention.
Figure 9:
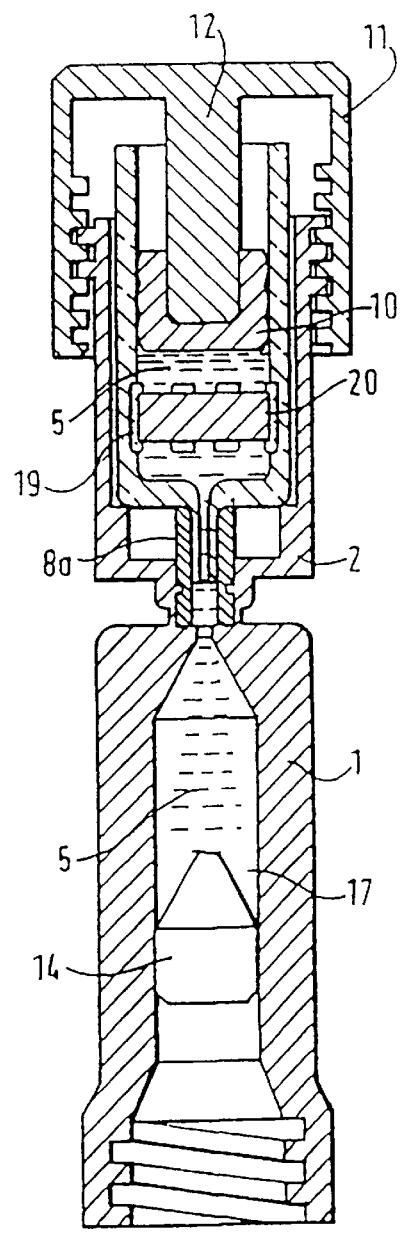

An alternative method of transferring the medicament is shown in FIGS. 8 and 9. An additional plunger 20 is assembled into the reservoir 4a, with the medicament 5 to be transferred contained between plungers 20 and 10. Seal 8a does not need to comprise a septum, because the piston prevents the medicament 5 from flowing into the injection component 1, even though the void 17a is in vacuum connection with void 17. If necessary, piston 20 may be prevented from moving as a result of a pressure differential by employing a stop or detent.

Referring to FIG. 9, the screw cap 11 is operated to move the rod 12 and plunger 10 towards the injection component. The medicament 5 is trapped between the pistons 10 and 20, and moves with the pistons until the wetted face of piston 20 reaches one or more grooves 19 in the wall of reservoir 4a. Piston 20 then stops because there is insufficient hydraulic pressure to move it, and the medicament 5 flows through the grooves 19 and into the injection component 1. The reservoir and associated parts are then detached as previously described and the injection component is ready for use.

Figure 10:
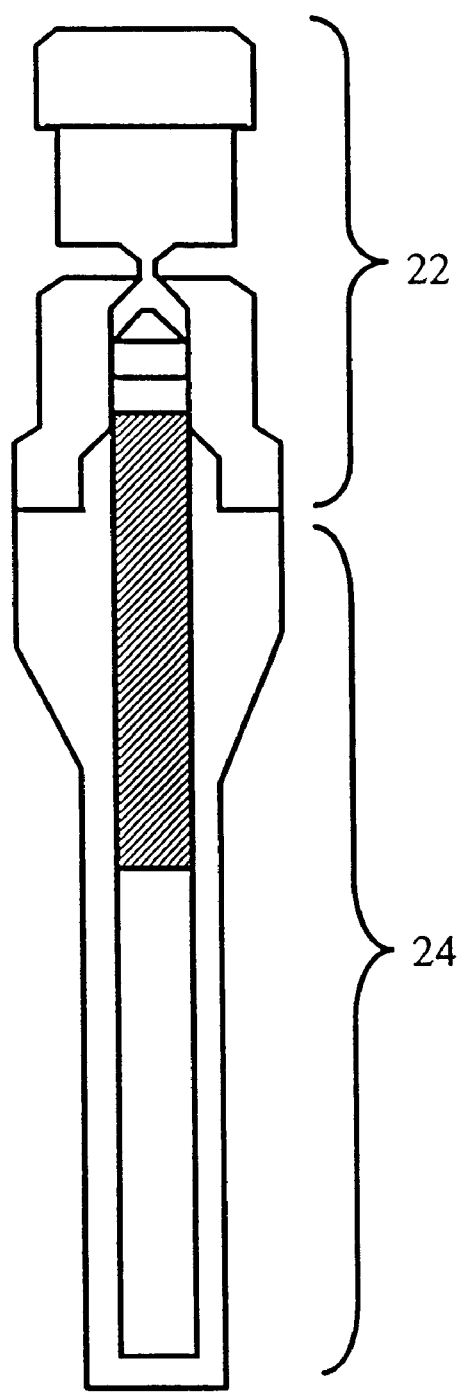
FIG. 10 is a schematic representation of an integral cartridge and power unit.

As shown schematically in FIG. 10, the cartridge 22 may be mounted on or made integral with the power unit or actuator 24. The actuator may be of any well known construction as described above or as shown and described, for example, in U.S. Pat. No. 5,891,086, issued Apr. 6, 1999.

What is claimed is:

1. A needleless injector cartridge, comprising:

an injection component defining a substantially evacuated void therein for receiving medicament, and having an injection discharge orifice communicating with the void; and a transfer device comprising a movable liquid-containing reservoir, and transfer means for causing the liquid to flow from the reservoir, through a reservoir outlet, into said void, wherein a septum is provided which, in an unpierced state, provides a barrier to flow of liquid into said void, and wherein said reservoir outlet is defined by means provided with a septum-piercing member movable with said reservoir.

2. A cartridge according to claim 1, wherein the said transfer means is arranged to cause the liquid to flow into the said void through the discharge orifice.

3. A cartridge according to claim 2, wherein the transfer device comprises a holder connected to the said injector component, the reservoir is movably mounted in the holder for movement towards the injection component, and said transfer means comprises a piston mounted for movement towards the reservoir outlet.

4. A cartridge according to claim 3, wherein the said transfer means further comprises a second piston, with the liquid being initially held between the two pistons, and at least one fluid path permitting fluid to escape from between the two pistons into the reservoir outlet once the pistons have reached a predetermined position.

5. A cartridge according to claim 3, wherein the said transfer means comprises a screw cap rotatable by a user to cause sliding movement of the piston.

6. A cartridge according to claim 6, wherein the screw cap has an internal screwthread which engages an external screwthread formed on the holder.

7. A cartridge according to claim 2, wherein the said void is in a substantially evacuated condition before liquid flows therein.

8. A cartridge according to claim 2, wherein the said void initially contains a medicament in lyophilised form, and the said liquid is a liquid suitable for reconstituting the drug from its lyophilised form into an injectable form.

9. A cartridge according to claim 2, wherein the said injection component has a piston therein which is initially located adjacent the discharge orifice, the piston being adapted to move away from the orifice in response to flow of liquid through the reservoir outlet.

10. A cartridge according to claim 2, wherein the said liquid is a liquid medicament in injectable form.

11. A cartridge according to claim 2, wherein the said injection component and the said transfer device are connected by a frangible connection.

12. A cartridge according to claim 1, wherein the said reservoir is of glass.

13. A cartridge according to claim 1, wherein the said void is defined by a plastics member.

14. A cartridge according to claim 1, wherein the void is defined by a liner surrounded by an outer member.

15. A needleless injector comprising a cartridge according to claim 1, mounted on an actuator.

16. A needleless injector according to claim 15, wherein the cartridge and actuator are integral with one another.

* * * * *